United States Patent [19]
Zoeller

[11] Patent Number: 5,977,407
[45] Date of Patent: Nov. 2, 1999

[54] PROCESS FOR ISOMERICALLY SELECTIVE HYDROCARBOXYLATION OF OLEFINS

[75] Inventor: Joseph Robert Zoeller, Kingsport, Tenn.

[73] Assignee: Eastman Chemical Company, Kingsport, Tenn.

[21] Appl. No.: 09/131,740

[22] Filed: Aug. 10, 1998

Related U.S. Application Data

[63] Continuation-in-part of application No. 08/599,489, Jan. 26, 1996, abandoned.

[51] Int. Cl.$^6$ ..................................................... C07C 51/14
[52] U.S. Cl. .............................................................. 562/522
[58] Field of Search ............................................. 562/522

[56] References Cited

U.S. PATENT DOCUMENTS

| | | |
|---|---|---|
| 3,579,552 | 5/1971 | Craddock et al. . |
| 3,641,074 | 2/1972 | Fenton . |
| 3,816,488 | 6/1974 | Craddock et al. . |
| 4,622,423 | 11/1986 | Burke . |
| 4,788,333 | 11/1988 | Burke . |
| 4,788,334 | 11/1988 | Burke . |

FOREIGN PATENT DOCUMENTS

| | | |
|---|---|---|
| 0 055 618 | 7/1982 | European Pat. Off. . |
| 0 495 548 A2 | 7/1992 | European Pat. Off. . |

*Primary Examiner*—Gary Geist
*Assistant Examiner*—Robert W. Deemie
*Attorney, Agent, or Firm*—Matthew W. Smith; Michael J. Blake; Harry J. Gwinnell

[57] ABSTRACT

Disclosed is a process for the preparation of an aliphatic carbonyl derivative compound having a normal:iso ratio of at least 3, and preferably 4, selected from aliphatic carboxylic acids, alkylesters of aliphatic carboxylic acids and anhydrides of aliphatic carboxylic acids by the hydrocarboxylation of terminal linear olefins in the presence of a catalyst system comprising (1) a rhodium containing compound, (2) a halide promoter selected from iodine, bromine and compounds thereof and (3) a trisubstituted organic compound of a group-15 element, preferably a phosphine or arsine. This process constitutes an improvement over known processes since it provides a one-step, lower pressure, higher reaction rate method of producing carboxylic acid derivatives having an increased normal:iso ratio in the absence of potentially hazardous chlorinated hydrocarbons and aromatic hydrocarbons.

19 Claims, No Drawings

PROCESS FOR ISOMERICALLY SELECTIVE HYDROCARBOXYLATION OF OLEFINS

This is a continuation-in-part application of application Ser. No. 08/599,489 filed Jan. 26, 1996, now abandoned.

This invention pertains to a process for the preparation of carboxylic acids and their related esters and anhydrides by the hydrocarboxylation of olefins. More specifically, this invention pertains to the preparation of carboxylic acids, esters and anhydrides having a normal:iso mole ratio of at least three. Even more specifically, this invention pertains to the isomerically selective preparation of carboxylic acids, esters and anhydrides by contacting carbon monoxide with a mixture of an α-olefin and a catalyst system comprising a rhodium-containing compound, a trisubstituted organic compound of a group-15 element and a halide promoter selected from iodine, bromine, and compounds thereof.

Carboxylic acids and their corresponding anhydrides and esters have a variety of uses in the chemical industry. Linear carboxylic acids and their related esters and anhydrides are especially useful in applications such as preservatives, synthetic lubricants, cosmetics, and cellulose esters used in the plastics industry. Current commercial uses of carboxylic acids and their derivatives primarily require linear acids instead of branched acids.

Most of the linear carboxylic acids having even numbers of carbons starting with decanoic (C-10) acid are directly available from natural oils where they are present in abundance as glyceride esters. In addition, very efficient processes are widely used for the generation of acetates from methanol and its derivatives.

However, demand for the intermediate acids (C-4 through C-9) is not being met by those sources, despite a growing need for these materials. Instead, the major volume of these intermediate length carboxylic acids are generated by either one of two methods. The first method consists of the sequential hydroformylation and oxidation of olefins, a two step process illustrated by equations (1) and (2):

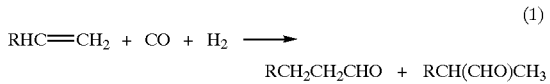

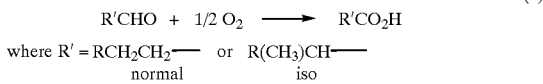

The second current commercial process involves the oxidation of butane or unsaturated natural acids. In both of these current commercial processes, the production of any derivatives of the carboxylic acids requires an additional chemical processing step. For example, butyrate esters can be made by esterification of butyric acid with alcohols, using a variety of catalysts. Butyric anhydride can be prepared from butyric acid by an exchange reaction with acetic anhydride.

Hydrocarboxylation, also referred to as hydrocarbonylation, is well known in the organic chemistry industry. The hydrocarboxylation reaction is illustrated by equation (3). This reaction represents a more direct, one step process for the intentional generation of carboxylic acids. Further, it offers the potential advantage of generating the ester and anhydride derivatives of the carboxylic acids directly from an olefin and carbon monoxide, without additional process steps, as further illustrated by equations (4), (5) and (6).

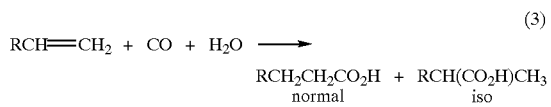

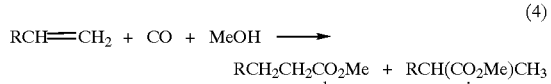

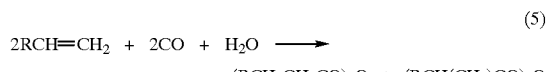

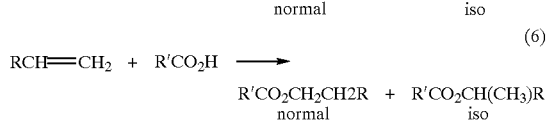

The reactions of equations (3), (4), (5) and (6) are well known in the field of organic chemistry as evidenced by Pino, et al., Organic Syntheses via Metal Carbonyls, Eds. I. Wender and P. Pino, Vol. 2, John Wiley & Sons, Inc., New York, N.Y., pages 233–296 (1977); Mullen, New Syntheses with Carbon Monoxide, Ed. J. Falbe, Springer-Verlag, Berlin, Germany, pages 275–286 (1980); Colquhoun, et al., Carbonylation—Direct Synthesis of Carbonyl Compounds, Plenum Press New York, N.Y., pages 102–106, 119–130 (1991); and Forster, et al., Catalysis Rev.—Sci. Eng., 23, 89 (1981). However, commercial application of hydrocarboxylation has been limited to the generation of propionic acid. The existing methods exhibit low isomeric selectivity, slow reaction rates and poor catalyst recovery. In addition, existing methods also require harsh reaction conditions.

Isomeric selectivity, as used throughout this application, is defined as the normal:iso mole ratio of the carboxylic acid, anhydride or ester reaction product containing one more carbon atom than the olefin reactant. For purposes of this application, "normal" refers to a carboxylic acid or carboxylic residue isomer which is unbranched at the alpha carbon and "iso" refers to a carboxylic acid isomer which is branched at the alpha carbon but unbranched at all other chain carbons. In addition to isomeric selectivity, it is also important to have a hydrocarboxylation method which has a high conversion level and is selective toward the production of total acids, anhydrides and/or esters as opposed to other possible oxidation products such as alcohols and ketones.

Noncommercial hydrocarboxylation processes using rhodium, iridium and palladium catalysts have been developed which require only moderate pressures and temperatures for the reactions of equations (3), (4), (5) and (6). See Pino, et al., Mullen, Colquhoun, et al., and Forster, et al cited in U.S. Pat. Nos. 3,579,551; 3,579,552; 3,816,488; 3,816,489; 3,818,060; 3,821,265 and 3,852,346, and in Bittler, et al., Ang. Chem., Int. Ed. 7, 329 (1968) and Tsuji, Organic Syntheses With Palladium Compounds, Springer-Verlag, Berlin, Germany, pages 81–84 (1980).

Rhodium catalysts have been found to show more selectivity toward the hydrocarboxylation reaction whereas other metal catalysts such as iron, cobalt and nickel produce a number of competing oxygenated products such as alcohols, aldehydes and ketones, in addition to carboxylic acids.

The most formidable of the current reaction problems involved with equations (3), (4), (5) and (6) is isomeric selectivity, where the normal isomer is commercially preferred, but existing catalyst systems result in unacceptable amounts of the iso acid derivatives. The hydrocarboxylation reaction naturally produces a mixture of normal and iso acid isomers. Since isomerism is not possible with propionic acid, selectivity is not an issue. Therefore, the existing methods are acceptable only for the production of propionic acid and it's derivatives. One of the most isomerically selective hydrocarboxylation processes described so far manipulates the percentage of normal carboxylic acid produced by varying the critical ratio of the iodide promoter to rhodium catalyst. But the best results shown in U.S. Pat. No. 3,816,488 are less than 70 mole percent n-heptanoic acid, as compared to total heptanoic acid produced, using a 3:1 I/Rh catalyst system wherein $RhCl_3 \cdot 3H_2O$ was used as the source of rhodium. That process is still not isomerically selective enough for commercial use. U.S. Pat. No. 4,788,334 discloses a method that reaches up to 87.8 percent isomeric selectivity toward n-heptanoic acid in an iodide promoted, $RhCl_3 \cdot 3H_2O$ catalyzed reaction wherein the critical component is an acetic acid accelerator. However, that method requires the use of large amounts of chlorinated hydrocarbons or aromatic hydrocarbon solvents which can be both hazardous and pose difficulties during the separation and refinement phase of production.

In a reaction somewhat similar to hydrocarboxylation, hydroformylation, the isomeric selectivity of rhodium catalyzed hydroformylation is manipulated with phosphines. However, references show that a rhodium/phosphine catalyzed system would not likewise add isomeric selectivity enhancement to hydrocarboxylation. U.S. Pat. No. 3,579,552 discloses an iodide promoted rhodium catalyst system in which a rhodium-containing phosphine ligand complex is one of the listed operable sources of rhodium which are taught to enhance the hydrocarboxylation reaction selectivity towards total carboxylic acids having one more carbon atom than the olefin reactant. No isomeric selectivity is shown. In fact, Example 22 of U.S. Pat. No. 3,579,552 discloses that the hydrocarboxylation of hexene-1 using a bis-triphenylphosphine complex $(RhCl(CO)(PPh_3)_2)$ as the catalyst precursor gave "similar" product distribution results to a non-phosphine containing process in which otherwise comparable reaction conditions were employed. The percent of C-7 normal isomer shown, as compared to total C-7 carboxylic acid produced is 29 percent. U.S. Pat. No. 3,579,552 shows that the addition of monodentate phosphines to an iodide promoted rhodium-containing catalyst system has neither a positive nor a negative effect on isomeric selectivity or on the percent conversion of olefin to total carboxylic acids.

Bidentate phosphine ligands have specifically been taught to be deleteriously interfering to isomeric selectivity in U.S. Pat. Nos. 4,788,333 and 4,788,334, which disclose the hydrocarboxylation and hydroesterification of 3-pentenoic acid using iodine promoted rhodium catalysts.

The present invention provides a process for the preparation of aliphatic carboxylic acids and their corresponding esters and anhydrides having a normal:iso mole ratio of at least 3. The process comprises contacting carbon monoxide with a mixture comprising:

(a) an α-olefin having at least 3 carbons;
(b) a nucleophile selected from the group consisting of water, alcohol and carboxylic acid;
(c) a catalyst system comprising components
  i) a rhodium containing compound;
  ii) a halide promoter selected from the group consisting of bromine, bromine compounds, iodine and iodine compounds; and
  iii) a trisubstituted organic compound of a group-15 element;

at a reaction pressure less than about 41 atmospheres (gauge) and a temperature from about 25 to 250° C., in the absence of chlorinated hydrocarbon solvents and aromatic hydrocarbon solvents.

I have discovered that the presence of a trisubstituted organic compound of a group-15 element, especially phosphines and arsines, in a halide-promoted, rhodium-catalyzed hydrocarboxylation system significantly enhances the isomeric selectivity and rate of reaction. Complexes containing monodentate phosphine ligands are disclosed in U.S. Pat. No. 3,579,552 as mere sources of rhodium for hydrocarboxylation with no effect on isomeric selectivity. I also have discovered that, despite previous disclosures in U.S. Pat. Nos. 4,788,333 and 4,788,334 that bidentate phosphines are deleterious to isomeric selectivity, bidentate phosphines and bidentate arsines do enhance isomeric selectivity as well as increase reaction rates.

The advantages and benefits provided by the present invention include (1) a commercially high normal:iso ratio of at least 3:1, preferably at least 4:1; (2) considerably lower pressure required than previous hydrocarboxylation methods, in fact, the isomeric selectivity is improved using lower pressures; (3) the esters and anhydrides of the carboxylic acids can be produced in an isomerically selective mixture by this one-step process by simply altering the nucleophilic reactant and the amounts of reactants—no additional steps are required; (4) increased reaction rates, especially when bidentate phosphines are used; (5) the trisubstituted group-15 compound increases the stability of the rhodium catalyst during separation of the product from the catalyst; and (6) the process is conducted in the absence of chlorinated hydrocarbon and aromatic hydrocarbon solvents.

The present hydrocarboxylation process is suitable using a wide range of α-olefins as the substrate. The α-olefin may contain terminal ethylenic unsaturation and may contain functionality, particularly those olefins containing carboxylates or a second olefinic double bond. Since adequate methods already exist for producing acetic acid, propionic acid and the naturally derived acids having more than ten carbons, this method is preferably applied to olefins containing 3 to 20 carbons, more preferably 3 to 10 carbons.

The other reactants in the present process are carbon monoxide and a nucleophilic compound selected from water, alcohol and carboxylic acid. The method of contacting the carbon monoxide with the mixture of other reactants and catalyst components is not new. The nucleophilic alcohol preferably is a linear alkanol containing 1–8 carbon atoms and the nucleophilic carboxylic acid preferably is a linear acid containing 2–9 carbon atoms. However, the nucleophilic carboxylic acid used for the production of an anhydride most preferably is the linear carboxylic acid having the number of carbons which would produce an acid anhydride having two identical alkyl chains. The "mirror image" anhydrides are far more valuable than are the "mixed" anhydrides in synthesis.

The catalyst system is comprised of a rhodium source, a halide promoter and a trisubstituted organic group-15 compound which will hereinafter be referred to as a ligand for convenience, regardless of whether the compound is part of a coordination complex or an independent uncoordinated compound. The rhodium component can be added in a variety of forms, including coordination complexes of phosphines, arsines, diphosphines, diarsines and other complexes. The complex may contain a halide which does or does not act as the halide promoter. However, it is preferred to add the ligand as a separate component since it requires an external synthetic step to generate the phosphine- or arsine-containing complexes. The most convenient, and currently lowest cost, source of rhodium is rhodium trichloride. However, it is useful in some applications to use Rh sources free of extraneous halides, so commercially available non-halide complexes such as dicarbonyl acetylacetonatorhodium ($Rh(CO)_2acac$) may be preferred in these applications. See U.S. Pat. Nos. 3,579,552 and 3,816,488 for a description of rhodium source compounds. The desirable overall Rh concentration in liquid media is from about 0.0001 to 0.1 mol/L with the preferred range being from about 0.001 to 0.01 mol/L.

The halide promoter component of the catalyst system can be bromine, iodine or compounds thereof. The promoter can be added in any number of forms such as, for example, an alkyl halide, an hydrogen halide, a salt such as a halide salt of a rhodium-containing complex or a salt of a group-15 ligand containing complex, elemental halide, as a ligand contained in a rhodium coordination compound, or any combination thereof.

Iodine and iodide compounds are preferred over bromine and bromides as the promoter. Iodide compounds such as hydrogen iodide, alkyl iodides and iodide salts are more preferred than elemental iodine. The hydrogen iodide and alkyl iodide are more preferred. The use of iodide salts is also feasible in some circumstances. See Table 2 following the examples where a series of examples in the presence of LiI are disclosed. With the notable exception, of 1,4-bis (diphenylphosphino)-butane (Example 27) the rate of reaction was not enhanced. However, with the exception of bis-diphenylphosphino-methane which consistently gave the lowest selectivity to the linear isomer, selectivity enhancements are consistently realized with the inclusion of Group 15 ligands. The halide promoter will hereinafter be referred to as an iodide for convenience.

The ratio of iodide to rhodium is not critical for improving the yield of carboxylic acids, enhancing the isomeric selectivity of the carboxylic acids or increasing the reaction rate. In the present invention, a large range of I/Rh atomic ratios is useful. However, it would be beneficial to use as low an I/Rh atomic ratio as feasible to minimize the potential of degrading the group-15 ligand. Therefore, although I/Rh atomic ratios of about 1:1 to 100:1 are applicable, the preferred level is in the range of about 3:1 to 15:1.

I have discovered that the addition of specific group-15 ligands to the iodide promoted hydrocarboxylation of olefins in the presence of rhodium markedly enhances isomeric selectivity and rate, as well as stabilizing the catalyst during the product separation stage. The group-15 containing ligand may be selected from a wide range of materials and may be represented by the general formulas:

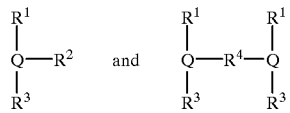

wherein Q is a group-15 atom such as arsenic and, especially, phosphorus; $R^1$, $R^2$ and $R^3$ are the same or different and each is hydrocarbyl containing up to about 12 carbon atoms; and $R^4$ is a hydrocarbylene group which links the 2 phosphorus atoms through a chain of 2 to 8 carbon atoms. Examples of the hydrocarbyl groups which $R^1$, $R^2$ and $R^3$ may represent include alkyl including aryl-substituted alkyl such as benzyl, cycloalkyl such as cyclohexyl, and aryl such as phenyl and phenyl substituted with one or more alkyl groups. Alkylene such as ethylene, trimethylene and hexamethylene, cycloalkylene such as cyclohexylene, and phenylene, naphthylene and biphenylene are examples of the hydrocarbylene groups which $R^4$ may represent. The choice of ligand which constitutes the best mode of operation for each application must balance differences in rate, selectivity and ligand availability. Monodentate phosphines and arsines have been found to promote the highest isomeric selectivity. However, the highest rates are achieved with diphosphines and diarsines containing 4 to 6 carbon units between the two group-15 elements. Phosphines and arsine are the preferred ligands because they demonstrate the highest enhancement of isomeric selectivity. However, the selectivity advantage assignable to the monodentate ligands, as compared to the bidentate ligands, is not substantial.

The preferred monodentate and bidentate phosphines are those most commercially available. Rhodium-containing phosphine or arsine complexes can be used, but an extra external synthetic step is required to generate those complexes. The scope of available monodentate phosphines is extensive, but the most commercially available, and therefore the preferred monodentate ligands, are numerous triarylphosphines and trialkylphosphines. Although the bidentate ligand is not restricted to aryl-containing ligands, those are preferred since they are most easily available. Examples include 1,4-bis-(diphenylphosphino)-butane, 1,5-bis-(diphenylphosphino)-pentane, and 1,6-bis-(diphenylphosphino)-hexane.

The concentration of ligand, like the concentration of halide promoter, is best determined as its proportion to the amount of rhodium. This ratio can vary over a wide range. However, excess ligand may lead to some deterioration in performance. Therefore, although the overall range of group-15 element:Rh mole atomic ratio may be from about 0.5:1 to 50:1, the preferred range is from about 1:1 to 10:1.

I have found that the isomeric selectivity of the iodide-promoted, rhodium-catalyzed hydrocarboxylation of α-olefins is dependent upon pressure when a group-15 ligand is not employed. See Comparison Examples 1–3 below. However, even at the higher pressures where selectivities to the normal isomer are becoming acceptable in the absence of a group-15 ligand, the addition of a carefully selected group-15 component gives superior results.

One of the key advantages of adding the trisubstituted group-15 component is that, unlike previous methods, neither higher pressures nor hydrogen is required to achieve good selectivities. On the contrary, improved rates and selectivities are observed at lower pressures and in the absence of hydrogen. The catalytic system described above has been operated at temperatures as low as 125° C. and 3 atmospheres (gauge) pressure, representing a partial pressure of CO of about 4 atmospheres absolute in a 1-pentene carbonylation, which was performed in the complete absence of hydrogen. See Example 32 below.

The minimum operable pressure is dependent upon a plurality of factors in addition to the presence of the group-15 ligand. For example, the minimum operable pressure is dependent upon the nature of the olefin being used since the olefin exerts a vapor pressure dependent upon chain length, temperature, the particular catalyst system employed and the concentration of the various catalyst components. Generally, the range of useful temperatures and pressures with this process is quite wide. The present process can be operated at a range of about 0.1 to 40 atmospheres (gauge), preferably about 1 to 30 atmospheres (gauge). The present hydrocarboxylation process generally may be carried out at temperatures in the range of about 25 to 250° C., preferably about 75 to 220° C.

The carbon monoxide may be employed in substantially pure form, as available commercially, but inert diluents such as carbon dioxide, nitrogen, methane, and noble gases can be present if desired. The presence of inert diluents does not affect the hydrocarboxylation reaction but their presence makes it necessary to increase the total pressure in order to maintain the desired CO partial pressure. The presence of minor amounts of water such as may be found in the commercial forms of the reactants is, however, entirely acceptable. The gas fed to the hydrocarboxylation process preferably comprises carbon monoxide containing up to about 50 volume percent hydrogen. The amount of hydrogen, however, should not be more than about 8 atmospheres partial pressure hydrogen, and preferably not more than about 5 atmospheres hydrogen. While the process may be carried out in the substantial absence of hydrogen, the presence of hydrogen has been found to have a favorable effect on the rate of hydrocarboxylation. However, this effect is limited to the amount of hydrogen necessary to reduce rhodium from its oxidized form (+3 oxidation state), to its reduced form (+1 oxidation state) and maintain rhodium in this lower oxidation state. Excessive hydrogen pressures (greater than 8–10 atm.) should be avoided since further, undesired, reduction products may be generated. (See, e.g., Organometallic Compounds, Vol. 1, pages 75–88; Wegman, U.S. Pat. No. 4,594,463; Knifton, U.S. Pat. No. 4,334,092.)

The process may be operated in a batch, semi-continuous or continuous mode. Hydrocarboxylation rates can be enhanced dramatically by using production systems designed for very efficient mass transfer, especially when light (C-3 and C-4) olefins are employed.

The process is carried out in the presence of an organic solvent or diluent such as, for example, carboxylic acids and esters and the like. However, this process is carried out in the absence of chlorinated hydrocarbons and aromatic hydrocarbons. In certain instances a material may serve as both solvent and reactant. For example, aliphatic carboxylic acid anhydrides may be prepared by the hydrocarboxylation of an olefin in the presence of a carboxylic acid under substantially anhydrous conditions. In this embodiment of the process, the carboxylic acid functions as both a process solvent and as a reactant. Mixtures of solvents can also be used, such as mixtures of propyl butyrate and butyric acid. The carboxylic acid solvent, when used, should preferably correspond to the acid, or the acid moiety of the anhydride, being produced since the preferred solvent is one that is indigenous to the system, e.g., butyric acid and/or propyl butyrate in the case of propylene hydrocarboxylation. When not a reactant or the product itself, the solvent or diluent preferably has a boiling point sufficiently different from the desired product in the reaction mixture so that it can be readily separated.

The isomerically selective hydrocarboxylation process of the present invention is further illustrated by the following examples of the hydrocarboxylation of 1-pentene. However, these examples are for illustration only and are in no way intended to restrict this process to the production of heptanoic acid or to any other aspect shown by the examples.

The following gas chromatography (GC) analyses were performed using a Hewlett Packard 5890 GC using a 75M (0.53 mm ID, 2.5 micron film) Quadrex 007 CMPS Capillary Column and nonane as an internal standard. A split injection was used to introduce the sample and sample detection was accomplished with TCD detector. The molar quantities of the various components were determined from the GC data using the following equation:

$$n_1 = \frac{X_i \cdot W_o}{MW_i[1 - (28X_{C6}/116)]}$$

wherein
n=moles of the component;
MW=molecular weight of the component;
X=weight fraction (obtained from GC analysis);
$X_{c6}$=Summation of weight fractions for C-6 acids;
$W_o$=initial weight of the solution.

The isomeric selectivity is expressed as the % linear isomer and was calculated by the equation:

% linear=(n-hexanoic acid/total C-6 acids).100% The normal:iso mole ratio thereafter was calculated by the equation:

normal:iso=% linear/(100 - % linear)

Rates are expressed as moles of C-6 acid produced per mole of Rh per hour often referred to in the literature as the turnover frequency (TOF) and were calculated as follows:

$$\text{Rate} = \text{TOF} = \frac{\text{Moles C-6 acid generated}}{\text{Moles Rh added} \cdot \text{Time of reaction in hours}}$$

All measurements of pressure were in atmospheres (gauge).

COMPARATIVE EXAMPLE 1

To a 300 mL Hastelloy® C autoclave equipped with an overhead stirrer and a high pressure liquid addition funnel was added 91.5 g of propionic acid (as solvent), 13.5 g (0.75 mol) of water, and 10 g of a 7.8% ethyl iodide in propionic acid. (0.78 g, 5 mmol of EtI). To this solution was added 0.129 g (0.5 mmol) of dicarbonyl acetylacetanatorhodium (I) as catalyst. The autoclave was sealed and thoroughly flushed with nitrogen and then with 5% hydrogen in CO. When all purging was complete, 35 g (0.5 moles) of 1-pentene was added via the liquid addition funnel. The autoclave was then pressurized to 1.7 atmospheres with hydrogen and carbon monoxide added to a final combined pressure of 6.8 atmospheres. The mixture was then heated with stirring to 190° C. without addition gas being added. Upon reaching temperature, the pressure was adjusted to 27.2 atmospheres using carbon monoxide. These conditions were maintained for 5 hrs feeding carbon monoxide upon demand. The autoclave was then cooled to <30° C. (to insure the 1-pentene remaining was not vaporized) and vented slowly. The reaction product was removed and a sample analyzed by GC. The results of this run are shown in Table I.

This example was run as a comparative standard for Examples 1–22. The only difference in this comparative run and Examples 1–22 is that this example contains no group-15 ligand.

This example illustrates that an "old method" hydrocarboxylation process operated at moderately low pressure and temperature has very low isomeric selectivity and slow rate of reaction.

EXAMPLE 1

The procedure in Comparative Example 1 was repeated except for the additional step of adding 0.262 g (1 mmol) of triphenylphosphine to the solution when the rhodium-containing catalyst was added. The results of this run are shown in Table I.

This example illustrates that the presence of $Ph_3P$ increases the selectivity by almost 100% more than the Comparative Example 1 and increases the rate by more than 5 times that of Comparative Example 1. This example also illustrates that the $Ph_3P$ ligand adds more selectivity than do the bidentate phosphines.

EXAMPLE 2

The procedure in Example 1 was repeated except the triphenylphosphine ligand was replaced by $Ph_2PCH_2PPh_2$ in a concentration ratio of 1:1 with rhodium. The results of this run are shown in Table 1.

This example shows that a bidentate phosphine having only 1 carbon unit between phosphines adds considerably less selectivity and slow rate than do the monodentate phosphines or diphosphines having more separation between phosphine groups which are shown in Table 1.

EXAMPLE 3

The procedure in Example 1 was repeated except that the triphenylphosphine ligand was replaced by $Ph_2P(CH_2)_2PPh_2$ in a concentration ratio of 1:1 with rhodium. The results are shown in Table 1.

EXAMPLE 4

The procedure in Example 1 was repeated except that the triphenylphosphine ligand was replaced by $Ph_2P(CH_2)_3PPh_2$ in a concentration ratio of 1:1 with rhodium. The results are shown in Table 1.

EXAMPLE 5

The procedure in Example 1 was repeated except that the triphenylphosphine ligand was replaced by $Ph_2P(CH_2)_4PPh_2$ in a concentration of 1:1 with rhodium. The results are shown in Table 1. This example illustrates that a bidentate phosphine having 4 carbon units between phosphines adds almost as much selectivity as $Ph_3P$ of Example 1, but at a greatly increased rate, a greater than 100% increase in rate. This ligand would be very useful in applications where a little selectivity could be spared for a faster rate.

EXAMPLE 6

The procedure in Example 1 was repeated except that the triphenylphosphine ligand was replaced by $Ph_2P(CH_2)_5PPh_2$ in a concentration ratio of 1:1 with rhodium. The results are shown in Table 1.

This example illustrates that a bidentate phosphine having 5 carbon units between phosphines enhances isomeric selectivity and reaction rate very similarly to its corresponding bidentate phosphine having 4 carbon units between phosphines (Example 5).

EXAMPLE 7

The procedure in Example 1 was repeated except that the triphenylphosphine ligand was replaced by $(cyclohexyl)_3P$ in a concentration ratio of 2:1 with rhodium. The results are shown in Table 1. This example shows that it is not necessary that the monodentate phosphine be aryl to increase selectivity. However, this ligand did little to increase the rate.

EXAMPLE 8

The procedure in Example 1 was repeated except that the concentration of the triphenylphosphine ligand was doubled. The results are shown in Table 1. This example illustrates that the ligand:rhodium ratio is critical for enhancing selectivity and rate. The 2:1 ratio of Example 1 adds much more selectivity and a somewhat faster rate.

COMPARATIVE EXAMPLE 2

The procedure in Comparative Example 1 was repeated except that the pressure was raised from 27.2 atmospheres to 34.0 atmospheres and the temperature was lowered from 190° C. to 175° C. The results are shown in Table 1. This example illustrates the effect of a moderately higher pressure and lower temperature on an "old method" hydrocarboxylation method. The selectivity was not effected, but the rate was increased by about 100%.

EXAMPLES 9–13

The following corresponding procedures were repeated for Examples 9–13 except that a moderately higher pressure (34.0 atmospheres) and lower temperature (175° C.) were maintained during each hydrocarboxylation process: compare procedures for Examples 9 with 1; 10 with 2; 11 with 3; 12 with 4; and 13 with 5. The results of each of these runs are shown in Table 1.

Examples 9–13 illustrate that the moderate increase of reaction pressure from 27.2 atmospheres to 34.0 atmospheres along with a slight decrease in temperature from 190° C. to 175° C. does not alter the isomeric selectivity of the process either positively or negatively. However, the reaction rates were fairly evenly scattered between a rate which is two times the rate of the corresponding lower pressure run and half the rate of the corresponding lower pressure run. The effect on rate seems to be specific for each ligand.

EXAMPLE 14

The procedure in Example 9 was repeated except that the triphenylphosphine was replaced by $Ph_2P(CH_2)_6PPh_2$ in a concentration ratio of 1:1 with rhodium. The results of this run are shown in Table 1. This example illustrates that a bidentate phosphine having 6 carbon units between phosphines enhances isomeric selectivity and especially reaction rate very well, similarly to its corresponding bidentate phosphine having 4 carbon units between phosphines.

EXAMPLE 15

The procedure in Example 9 was repeated except that the triphenylphosphine was replaced by triphenylarsine. The results of this run are shown in Table 1. This example illustrates that a monodentate aryl arsine enhances reaction rate similarly to its corresponding monodentate aryl phosphine but enhances isomeric selectivity somewhat less than the arsine, comparing this example with Example 9.

COMPARATIVE EXAMPLE 3

The procedure in Comparative Example 1 was repeated except that the pressure was raised from 27.2 atmospheres to 51.0 atmospheres. The results are shown in Table 1. This example illustrates the effect of a much higher pressure on an "old method" hydrocarboxylation method, when compared to Comparative Example 1. The selectivity was significantly increased and the rate was increased somewhat. This example shows that isomeric selectivity of iodide promoted rhodium catalyzed hydrocarboxylation processes without the presence of a group-15 ligand is pressure dependant.

EXAMPLES 16–21

The following corresponding procedures were repeated for Examples 16–21 except that a much higher pressure (51.0 atmospheres) was maintained during each hydrocarboxylation process: compare procedures for Examples 16 with 1; 17 with 3; 18 with 4; 19 with 5; 20 with 6. The procedure for Example 21 was the same as the procedure for Example 14 except that the pressure was maintained at 51.0 atmospheres (instead of 34.0 atmospheres) and the temperature was maintained at 190° C. (instead of 175° C.). The results of each of these runs are shown in Table 1.

Examples 16–21 illustrate that a large increase of pressure from 27.2 atmospheres to 51.0 atmospheres in the present group-15 ligand containing hydrocarboxylation process has a definite consistent negative effect on isomeric selectivity. The effect of the large increase of pressure on rate is ligand specific.

Examples 19–21, when compared to Examples 5, 6, 13 and 14, illustrate that the bidentate phosphines having 4 to 6 carbon units between phosphines definitely respond to changed conditions in a similarly way. The process enhancement gained by these three diphosphines is quite distinguishable from that of the monodentate phosphines.

EXAMPLE 22

The procedure of Example 15 was repeated except that the pressure was maintained at 51.0 atmospheres and the temperature was maintained at 190° C. The results are shown in Table 1. This example illustrates that triphenylarsine does not effect a similar rate as does triphenylphosphine under 51.0 atmospheres like it did under 34.0 atmospheres in Example 15. Therefore, the similarity between the effect from arsines and phosphines may greatly depend upon pressure and temperature. This example also shows that triphenylarsine displayed an actual increase in isomeric selectivity when the conditions were changed from 34.0 atmospheres and 175° C. to 51.0 atmospheres and 190° C.

Examples 23–31 and Comparative Example 4 were run to illustrate the effect of using an iodide salt (LiI) instead of the methyl iodide which was used as the halide promoter in Examples 1–22 as part of the catalyst system for the present process. These reactions were run using the same procedure as Example 1 except that 0.134 g (1 mmol) of LiI was substituted for ethyl iodide and the group-15 ligand was varied as indicated below:

COMPARATIVE EXAMPLE 4

The addition of a group-15 ligand was omitted from this procedure. The results are shown in Table II.

This example, when compared to Comparative Example 1, illustrates the effect that the substitution of lithium iodide for the ethyl iodide has on an "old method" iodide promoted rhodium catalyzed hydrocarboxylation process in the absence of a group-15 ligand. The iodide salt significantly increased the isomeric selectivity and the rate.

EXAMPLES 23–31

These examples were prepared following the procedures of their corresponding examples in Table I except for the substitution of LiI for $C_2H_5I$: corresponding examples 23 to 1; 24 to 2; 25 to 3; 26 to 4; 27 to 5; 28 to 6; 30 to 7; and 31 to 8. There is no directly corresponding example for Example 29 in Table I. However, Example 29 was prepared following the procedure for Example 23 except that the triphenylphosphine was replaced with $Ph_2P(CH_2)_6PPh_2$ in a concentration ratio of 1:1 with rhodium. The results from each of the Examples 23–31 are shown in Table II.

Examples 23–31, when compared to Comparative Example 4, illustrate that the inclusion of a group-15 ligand in a rhodium catalyzed hydrocarboxylation process promoted by an iodide salt does not generally improve the reaction rate. However, it does consistently enhance the isomeric selectivity, with the exception of the bidentate phosphine having a single carbon unit separating two phosphines (Example 24).

TABLE I

| Ex. No. | Group 15 Ligand | Ligand to Rh Ratio | Temp. (° C.) | Press. (atm) | Selectivity (% linear) (normal:iso) | Rate (mol C-6 acid/ Rh/hr) |
|---|---|---|---|---|---|---|
| C-1 | none | — | 190 | 27.2 | 49% (1.0) | 11 |
| 1 | $Ph_3P$ | 2 | 190 | 27.2 | 87% (6.7) | 56 |
| 2 | $Ph_2PCH_2PPh_2$ | 1 | 190 | 27.2 | 70% (2.3) | 16 |
| 3 | $Ph_2P(CH_2)_2PPh_2$ | 1 | 190 | 27.2 | 82% (4.6) | 15 |
| 4 | $Ph_2P(CH_2)_3PPh_2$ | 1 | 190 | 27.2 | 80% (4.0) | 36 |
| 5 | $Ph_2P(CH_2)_4PPh_2$ | 1 | 190 | 27.2 | 82% (4.6) | 135 |
| 6 | $Ph_2P(CH_2)_5PPh_2$ | 1 | 190 | 27.2 | 82% (4.6) | 114 |
| 7 | $(cyclohexyl)_3P$ | 2 | 190 | 27.2 | 82% (4.6) | 12 |
| 8 | $Ph_3P$ | 4 | 190 | 27.2 | 83% (4.9) | 42 |
| C-2 | none | — | 175 | 34.0 | 49% (1.0) | 21 |
| 9 | $Ph_3P$ | 2 | 175 | 34.0 | 87% (6.7) | 44 |
| 10 | $Ph_2PCH_2PPh_2$ | 1 | 175 | 34.0 | 70% (2.3) | 30 |
| 11 | $Ph_2P(CH_2)_2PPh_2$ | 1 | 175 | 34.0 | 82% (4.6) | 16 |
| 12 | $Ph_2P(CH_2)_3PPh_2$ | 1 | 175 | 34.0 | 80% (4.0) | 48 |
| 13 | $Ph_2P(CH_2)_4PPh_2$ | 1 | 175 | 34.0 | 82% (4.6) | 60 |
| 14 | $Ph_2P(CH_2)_6PPh_2$ | 1 | 175 | 34.0 | 82% (4.6) | 99 |
| 15 | $Ph_3As$ | 2 | 175 | 34.0 | 74% (2.8) | 43 |
| C-3 | none | — | 190 | 51.0 | 72% (2.6) | 29 |
| 16 | $Ph_3P$ | 2 | 190 | 51.0 | 75% (3.0) | 80 |
| 17 | $Ph_2P(CH_2)_2PPh_2$ | 1 | 190 | 51.0 | 72% (2.6) | 58 |
| 18 | $Ph_2P(CH_2)_3PPh_2$ | 1 | 190 | 51.0 | 74% (2.8) | 25 |
| 19 | $Ph_2P(CH_2)_4PPh_2$ | 1 | 190 | 51.0 | 66% (1.9) | 92 |
| 20 | $Ph_2P(CH_2)_5PPh_2$ | 1 | 190 | 51.0 | 74% (2.8) | 107 |
| 21 | $Ph_2P(CH_2)_6PPh_2$ | 1 | 190 | 51.0 | 78% (3.5) | 82 |
| 22 | $Ph_3As$ | 2 | 190 | 51.0 | 89% (8.1) | 43 |

When compared to the corresponding Examples 1–8, Examples 23–31 also illustrate that the isomeric selectivity enhancement is generally decreased by the presence of a LiI promoter, instead of an ethyl iodide promoter, except for when bis-diphenylphosphinoheptane is the ligand (Example 26). The differences in rate caused by the choice of LiI or ethyl iodide seem to be highly specific upon the choice of ligand.

It is interesting to note that Examples 27–30, the samples containing bidentate phosphines having 4 to 6 carbon units between phosphines, did not react very similarly, as they did in the ethyl iodide promoted systems in Examples 5, 6, 13, 14, 19, 20 and 21.

TABLE II

| Ex. No. | Group 15 Ligand | Ligand to Rh Ratio | Temp. (° C.) | Press. (atm) | Selectivity (% linear) (normal:iso) | Rate (mol C-6 acid/ Rh/hr) |
|---|---|---|---|---|---|---|
| C-4 | none | — | 190 | 27.2 | 70% (2.3) | 69 |
| 23 | $Ph_3P$ | 2 | 190 | 27.2 | 84% (5.2) | 76 |
| 24 | $Ph_2PCH_2PPh_2$ | 1 | 190 | 27.2 | 58% (1.4) | 13 |
| 25 | $Ph_2P(CH_2)_2PPh_2$ | 1 | 190 | 27.2 | 77% (3.3) | 39 |
| 26 | $Ph_2P(CH_2)_3PPh_2$ | 1 | 190 | 27.2 | 86% (6.1) | 28 |
| 27 | $Ph_2P(CH_2)_4PPh_2$ | 1 | 190 | 27.2 | 76% (3.2) | 96 |
| 28 | $Ph_2P(CH_2)_5PPh_2$ | 1 | 190 | 27.2 | 75% (3.0) | 58 |
| 29 | $Ph_2P(CH_2)_6PPh_2$ | 1 | 190 | 27.2 | 81% (4.3) | 18 |
| 30 | $(cyclohexyl)_3P$ | 2 | 190 | 27.2 | 75% (3.0) | 40 |
| 31 | $Ph_3P$ | 4 | 190 | 27.2 | 76% (3.2) | 28 |

EXAMPLE 32

To a 100 mL thick-wall glass pressure bottle was added 30.7 g of propionic acid and 1.8 g of water (0.1 mol). The mixture was thoroughly flushed with argon to remove oxygen from the solution. To the argon purged solution was added 0.68 g of 47% aqueous HI, 0.13 g of dicarbonyl acetylacetanatorhodium (I) (0.5 mmol), and 0.22 g of 1,4-bis-(diphenylphosphino)-butane (0.5 mmol) as catalyst and 3.5 g (50 mmol) of 1-pentene. (The catalyst formed a precipitate upon bringing all the materials in contact, but the reaction still proceeded.) The system was connected to a regulated carbon monoxide source and flushed thoroughly with CO by pressurizing to 3 atmospheres with CO and venting four times. The vessel was pressurized to 2.5 atmospheres and then immersed in a 125° C. oil bath. The pressure rose to about 3.3 atmospheres and then started dropping. Carbon monoxide was added continually to maintain a pressure of 3.3 atmospheres for 7 hrs. at which time gas uptake had slowed considerably. The mixture was cooled and samples of the mixture were analyzed for C-6 acids by GC. (Rates were not measured in this case.) The mixture analyzed as 11.4% hexanoic (normal) acid and 3.9% branched C-6 acids, which represents a selectivity of 74.5% for the normal isomer.

For comparison, the reaction above was repeated exactly, except the diphosphine ligand was omitted. (No precipitate formed in the absence of the diphosphine.) The mixture analyzed as 6.5% hexanoic acid and 9.5% branched C-6 acids. This represents a selectivity of only 41% for the normal isomer.

This example demonstrates the positive effect on selectivity for these systems at lower temperatures and pressures, as well as the selectivity enhancement added by the presence of bis-diphenylphosphinobutane.

The invention has been described in detail with particular reference to preferred embodiments thereof, but it will be understood that variations and modifications can be effected within the spirit and scope of the invention.

I claim:

1. Process for the preparation of an aliphatic carbonyl derivative compound having a normal:iso ratio of at least 3:1, selected from aliphatic carboxylic acids, alkyl esters of aliphatic carboxylic acids and anhydrides of aliphatic carboxylic acids comprising contacting carbon monoxide with a mixture comprising
   (a) an α-olefin having at least 3 carbons;
   (b) a nucleophile selected from the group consisting of water, alcohol and carboxylic acid;
   (c) a catalyst system comprising components
       i) a rhodium containing compound;
       ii) a halide promoter selected from the group consisting of bromine, bromine compounds, iodine and iodine compounds; and
       (iii) a trisubstituted organic compound of a group-15 element;
   at a pressure of from about 1 to 40 atmospheres (gauge), which includes a hydrogen partial pressure of not more than about 5 atmospheres, and a temperature of from about 25 to 250° C., in the absence of chlorinated hydrocarbons and aromatic hydrocarbons.

2. Process according to claim 1 wherein the reaction pressure is from about 1 to 30 atmospheres (gauge) and the temperature is from about 75 to 220° C.

3. Process according to claim 1 wherein said aliphatic carbonyl compound has a normal : iso ratio of at least 4:1.

4. Process according to claim 1 wherein said rhodium containing compound is present in a concentration of from about 0.0001 to 0.1 mol/L, said halide promoter is present in a halide:rhodium atomic ratio of from about 1:1 to 100:1, and said trisubstituted group-15 compound is present in a group-15 element:rhodium atomic ratio of from about 0.5:1 to 50:1.

5. Process according to claim 4 wherein said rhodium containing compound is present in a concentration of from about 0.001 to 0.01 mol/L, said halide promoter is present in a halide:rhodium atomic ratio of from about 3:1 to 15:1, and said trisubstituted group-15 compound is present in a group-15 element:rhodium atomic ratio of from about 1:1 to 10:1.

6. Process according to claim 1 wherein said rhodium containing compound is selected from the group consisting of rhodium salts, rhodium containing coordination complexes of phosphines, rhodium containing coordination complexes of arsines, rhodium containing coordination complexes of diphosphines and rhodium containing coordination complexes of diarsines.

7. Process according to claim 6 wherein said rhodium containing compound is selected from the group consisting of rhodium trichloride and dicarbonyl acetylacetonatorhodium (Rh(CO)$_2$acac).

8. Process according to claim 1 wherein said halide promoter is an iodide.

9. Process according to claim 8 wherein said iodide is selected from the group consisting of hydrogen iodide, alkyl iodides and iodide salts.

10. Process according to claim 1 wherein said trisubstituted group-15 compound is selected from the group consisting of phosphines, arsines, diphosphines and diarsines.

11. Process according to claim 10 wherein said diphosphines contain about 4 to 6 carbon units between phosphorous atoms and said diarsines contain about 4 to 6 carbon units between arsenic atoms.

12. Process according to claim 11 wherein said phosphine is selected from the group consisting of triarylphosphines and alkylphosphines, and said diphosphine is selected from the group consisting of 1,4-bis-(diphenylphosphino)-butane, 1,5-bis-(diphenylphosphino)-pentane and 1,6-bis-(diphenylphosphino)-hexane.

13. Process of claim 1 wherein said nucleophile is water and the aliphatic carbonyl derivative compound produced is a carboxylic acid.

14. Process of claim 1 wherein said nucleophile is a carboxylic acid and the aliphatic carbonyl derivative compound produced is an anhydride of a carboxylic acid.

15. Process of claim 1 wherein said nucleophile is water and the aliphatic carbonyl derivative compound produced is an anhydride of a carboxylic acid.

16. Process of claim 1 wherein said nucleophile is an alcohol and the aliphatic carbonyl derivative compound produced is an ester of a carboxylic acid.

17. Process of claim 1 wherein the hydrogen gas is present at a partial pressure of less than about 1.7 atmospheres.

18. Process of claim 1 wherein the process is carried out in the substantial absence of added hydrogen gas.

19. Process for the preparation of an aliphatic carbonyl derivative compound having a normal:iso ratio of at least 3:1, selected from aliphatic carboxylic acids, alkyl esters of aliphatic carboxylic acids and anhydrides of aliphatic carboxylic acids comprising contacting a mixture comprising (a) an α-olefin having at least 3 carbons;
(b) a nucleophile selected from the group consisting of water, alcohol and carboxylic acid;
(c) a catalyst system comprising
  i) a rhodium containing compound;
  ii) a halide promoter selected from the group consisting of bromine, bromine compounds, iodine and iodine compounds; and
  (iii) a trisubstituted phosphine or arsine compound; with a gas feed consisting essentially of carbon monoxide at a pressure of from about 1 to 40 atmospheres (gauge), including a hydrogen partial pressure of not more than about 5 atmospheres, and a temperature of from about 25 to 250° C., in the absence of chlorinated hydrocarbons and aromatic hydrocarbons.

* * * * *